(12) United States Patent
Bloomfield

(10) Patent No.: US 9,978,575 B2
(45) Date of Patent: May 22, 2018

(54) GROUPING AMPLITUDES OF TOF EXTRACTIONS TO DETECT CONVOLUTION DUE TO RESOLUTION SATURATION

(71) Applicant: DH Technologies Development Pte. Ltd., Singapore (SG)

(72) Inventor: Nic G. Bloomfield, Newmarket (CA)

(73) Assignee: DH Technologies Development Pte. Ltd., Singapore (SG)

( * ) Notice: Subject to any disclaimer, the term of this patent is extended or adjusted under 35 U.S.C. 154(b) by 0 days. days.

(21) Appl. No.: 15/513,267

(22) PCT Filed: Sep. 21, 2015

(86) PCT No.: PCT/IB2015/057263
§ 371 (c)(1),
(2) Date: Mar. 22, 2017

(87) PCT Pub. No.: WO2016/055889
PCT Pub. Date: Apr. 14, 2016

(65) Prior Publication Data
US 2017/0250065 A1    Aug. 31, 2017

Related U.S. Application Data

(60) Provisional application No. 62/061,496, filed on Oct. 8, 2014.

(51) Int. Cl.
*H01J 49/40* (2006.01)
*G01N 27/62* (2006.01)
(Continued)

(52) U.S. Cl.
CPC .............. *H01J 49/40* (2013.01); *G01N 27/62* (2013.01); *H01J 49/0036* (2013.01); *H01J 49/26* (2013.01); *H01J 49/04* (2013.01)

(58) Field of Classification Search
CPC ........ H01J 49/0036; H01J 49/26; H01J 49/40; G01N 27/62
See application file for complete search history.

(56) References Cited

U.S. PATENT DOCUMENTS 7,084,393 B2 * 8/2006 Fuhrer ................ H01J 49/0036
250/283
2010/0001180 A1 * 1/2010 Bateman ............. H01J 49/0036
250/282
(Continued)

FOREIGN PATENT DOCUMENTS

WO    2013061144 A1    5/2013

OTHER PUBLICATIONS

International Search Report and Written Opinion for PCT/IB2015/057263, dated Jan. 12, 2016.

*Primary Examiner* — Eliza Osenbaugh-Stewart
(74) *Attorney, Agent, or Firm* — John R. Kasha; Kelly L. Kasha; Kasha Law LLC

(57) ABSTRACT

Sample molecules are ionized producing a beam of ions using an ion source. A plurality of ion extractions are performed on the beam of ions using a TOF mass spectrometer. Electrical detections from each extraction are measured using an ADC, producing a mass sub-spectrum for each extraction. An ion m/z from the plurality of mass sub-spectra is selected. For each mass sub-spectrum, the amplitude and m/z of an ion within a m/z tolerance of the ion m/z is assigned to the corresponding amplitude band of a plurality of predetermined amplitude bands, producing a plurality of amplitude and m/z values for the each amplitude band. For each amplitude band of the plurality of predetermined amplitude bands, the plurality of amplitude and m/z values are combined into a peak, resulting in a plurality of peaks corresponding to the plurality of predetermined amplitude bands.

15 Claims, 12 Drawing Sheets

(51) Int. Cl.
*H01J 49/26* (2006.01)
*H01J 49/00* (2006.01)
*H01J 49/04* (2006.01)

(56) References Cited

U.S. PATENT DOCUMENTS

| | | |
|---|---|---|
| 2011/0186727 A1 | 8/2011 | Loboda |
| 2012/0193526 A1 | 8/2012 | Kovtoun |
| 2013/0048852 A1 | 2/2013 | Verenchikov |

* cited by examiner

GROUPING AMPLITUDES OF TOF EXTRACTIONS TO DETECT CONVOLUTION DUE TO RESOLUTION SATURATION

CROSS REFERENCE TO RELATED APPLICATION

This application claims the benefit of U.S. Provisional Patent Application Ser. No. 62/061,496, filed Oct. 8, 2014, the content of which is incorporated by reference herein in its entirety.

INTRODUCTION

The ion detection system used with a time-of-flight (TOF) mass spectrometer, for example, can include an ion detector and an analog-to-digital converter (ADC). The TOF mass spectrometer performs a plurality of ion extractions on a beam of ions of one or more mass-to-charge ratios (m/z) received from an ion source. For each extraction, the ion detector generates an electrical detection pulse for every ion that strikes it. The ADC provides a value that relates to the average amplitude of electrical detections received at any one time. By measuring the time at which the electrical detections are received by the ADC, the TOF mass spectrometer provides a mass analysis of each extraction. This mass analysis produces, for example, a sub-spectrum for each extraction. Conventionally, a mass spectrum for a plurality of ion extractions is obtained by combining (i.e., summing) the sub-spectra for the plurality of extractions.

This method works well up to a certain point. However, when a large number of ions of the same m/z hit the detector at approximately the same time it becomes difficult to resolve or observe nearby ions. This effect on the mass spectrum can be called resolution saturation and results in convolution of some peaks such that the individual components cannot be distinguished even though the resolution determined from the observed peak appears sufficient to do so.

SUMMARY

A system is disclosed for grouping and combining amplitudes for a selected ion m/z from TOF sub-spectra in order to detect convolution. An ion source ionizes sample molecules producing a beam of ions. A TOF mass spectrometer that includes a detector performs a plurality of ion extractions on the beam of ions. An ADC receives electrical detections from the detector and, during each extraction, measures the amplitudes of the ions hitting the detector over time, producing a mass sub-spectrum for each extraction of the plurality of ion extractions. A processor in communication with the TOF mass spectrometer and the ADC receives the plurality of mass sub-spectra. The processor selects an ion m/z from the plurality of mass sub-spectra. For each mass sub-spectrum of the plurality of mass sub-spectra, the processor assigns the amplitude and m/z of an ion within a m/z tolerance of the ion m/z to the corresponding amplitude band of a plurality of predetermined amplitude bands, producing a plurality of amplitude and m/z values for the each amplitude band. For each amplitude band of the plurality of predetermined amplitude bands, the processor combines the plurality of amplitude and m/z values into a peak, resulting in a plurality of peaks corresponding to the plurality of predetermined amplitude bands.

A method is disclosed for grouping and combining amplitudes for a selected ion m/z from TOF sub-spectra in order to detect convolution. Sample molecules are ionized producing a beam of ions using an ion source. A plurality of ion extractions are performed on the beam of ions using a TOF mass spectrometer that includes a detector. Electrical detections from the detector for the plurality of ion extractions are received and, during each extraction, the amplitudes of the ions hitting the detector over time are measured using an ADC, producing a mass sub-spectrum for each extraction of the plurality of ion extractions. The plurality of mass sub-spectra are received using a processor. An ion m/z from the plurality of mass sub-spectra is selected using the processor. For each mass sub-spectrum of the plurality of mass sub-spectra, the amplitude and m/z of an ion within a m/z tolerance of the ion m/z is assigned to the corresponding amplitude band of a plurality of predetermined amplitude bands using the processor, producing a plurality of amplitude and m/z values for the each amplitude band. For each amplitude band of the plurality of predetermined amplitude bands, the plurality of amplitude and m/z values are combined into a peak using the processor, resulting in a plurality of peaks corresponding to the plurality of predetermined amplitude bands.

A computer program product is disclosed whose contents include a program with instructions being executed on a processor so as to perform a method for grouping and combining amplitudes for a selected ion m/z from TOF sub-spectra in order to detect convolution. This method is performed by a system that includes one or more distinct software modules. These distinct software modules include a control module and an analysis module.

The control module instructs an ion source to ionize sample molecules producing a beam of ions. The control module instructs a TOF mass spectrometer that includes a detector to perform a plurality of ion extractions on the beam of ions. The control module instructs an ADC to receive electrical detections from the detector for the plurality of ion extractions and, during each extraction, measure the amplitudes of the ions hitting the detector over time, producing a mass sub-spectrum for each extraction of the plurality of ion extractions.

The analysis module receives the plurality of mass sub-spectra. The analysis module selects an ion m/z from the plurality of mass sub-spectra. For each mass sub-spectrum of the plurality of mass sub-spectra, the analysis module assigns the amplitude and m/z of an ion within a m/z tolerance of the ion m/z to the corresponding amplitude band of a plurality of predetermined amplitude bands, producing a plurality of amplitude and m/z values for the each amplitude band. For each amplitude band of the plurality of predetermined amplitude bands, the analysis module, combines the plurality of amplitude and m/z values into a peak, resulting in a plurality of peaks corresponding to the plurality of predetermined amplitude bands.

BRIEF DESCRIPTION OF THE DRAWINGS

The skilled artisan will understand that the drawings, described below, are for illustration purposes only. The drawings are not intended to limit the scope of the present teachings in any way.

Figure 1:
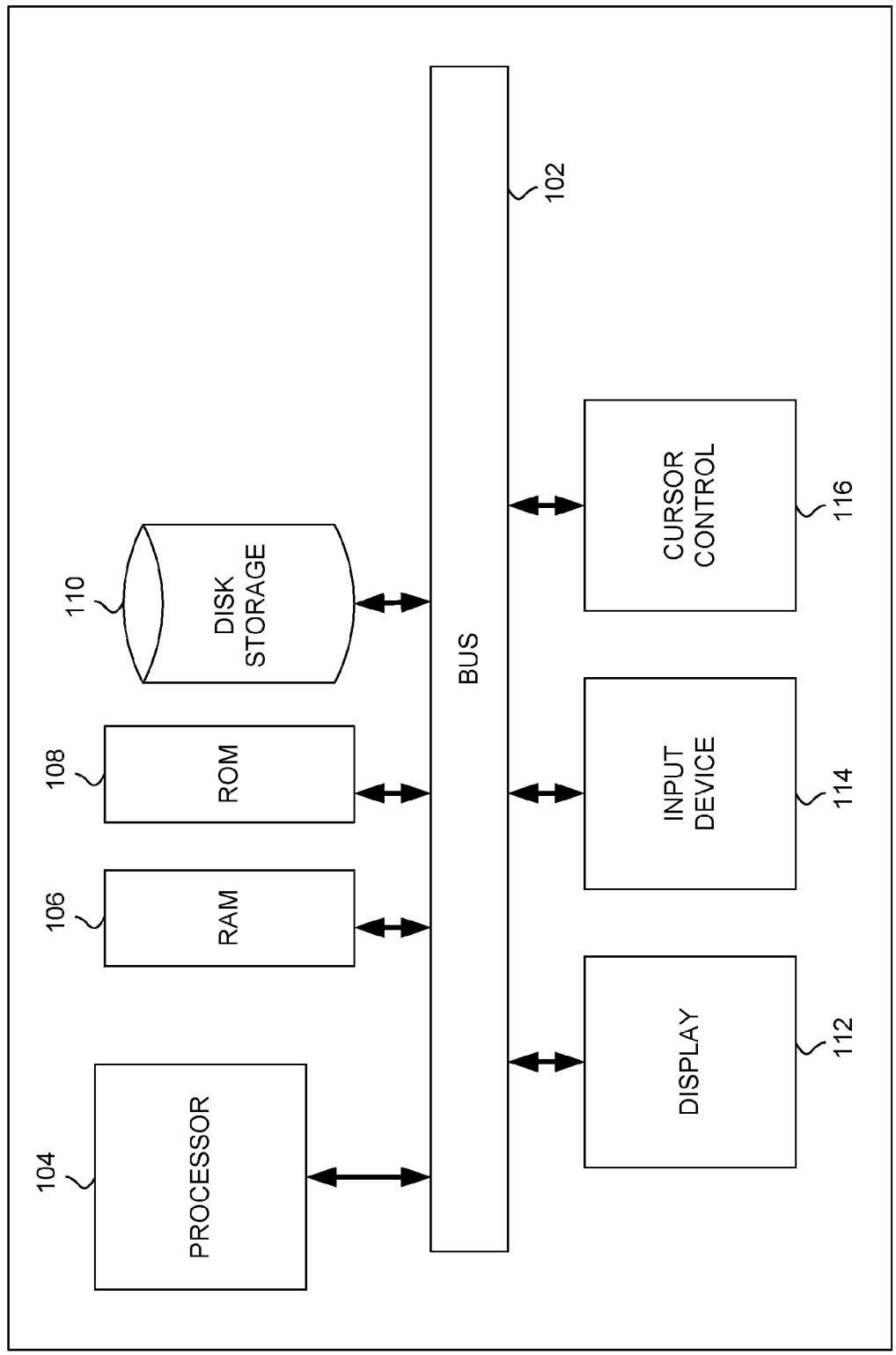
FIG. 1 is a block diagram that illustrates a computer system, upon which embodiments of the present teachings may be implemented.

Before one or more embodiments of the present teachings are described in detail, one skilled in the art will appreciate that the present teachings are not limited in their application to the details of construction, the arrangements of components, and the arrangement of steps set forth in the following detailed description or illustrated in the drawings. Also, it is to be understood that the phraseology and terminology used herein is for the purpose of description and should not be regarded as limiting.

DESCRIPTION OF VARIOUS EMBODIMENTS

Computer-Implemented System

FIG. 1 is a block diagram that illustrates a computer system 100, upon which embodiments of the present teachings may be implemented. Computer system 100 includes a bus 102 or other communication mechanism for communicating information, and a processor 104 coupled with bus 102 for processing information. Computer system 100 also includes a memory 106, which can be a random access memory (RAM) or other dynamic storage device, coupled to bus 102 for storing instructions to be executed by processor 104. Memory 106 also may be used for storing temporary variables or other intermediate information during execution of instructions to be executed by processor 104. Computer system 100 further includes a read only memory (ROM) 108 or other static storage device coupled to bus 102 for storing static information and instructions for processor 104. A storage device 110, such as a magnetic disk or optical disk, is provided and coupled to bus 102 for storing information and instructions.

Computer system 100 may be coupled via bus 102 to a display 112, such as a cathode ray tube (CRT) or liquid crystal display (LCD), for displaying information to a computer user. An input device 114, including alphanumeric and other keys, is coupled to bus 102 for communicating information and command selections to processor 104. Another type of user input device is cursor control 116, such as a mouse, a trackball or cursor direction keys for communicating direction information and command selections to processor 104 and for controlling cursor movement on display 112. This input device typically has two degrees of freedom in two axes, a first axis (i.e., x) and a second axis (i.e., y), that allows the device to specify positions in a plane.

A computer system 100 can perform the present teachings. Consistent with certain implementations of the present teachings, results are provided by computer system 100 in response to processor 104 executing one or more sequences of one or more instructions contained in memory 106. Such instructions may be read into memory 106 from another computer-readable medium, such as storage device 110. Execution of the sequences of instructions contained in memory 106 causes processor 104 to perform the process described herein. Alternatively hard-wired circuitry may be used in place of or in combination with software instructions to implement the present teachings. Thus implementations of the present teachings are not limited to any specific combination of hardware circuitry and software.

In various embodiments, computer system 100 can be connected to one or more other computer systems, like computer system 100, across a network to form a networked system. The network can include a private network or a public network such as the Internet. In the networked system, one or more computer systems can store and serve the data to other computer systems. The one or more computer systems that store and serve the data can be referred to as servers or the cloud, in a cloud computing scenario. The one or more computer systems can include one or more web servers, for example. The other computer systems that send and receive data to and from the servers or the cloud can be referred to as client or cloud devices, for example.

The term "computer-readable medium" as used herein refers to any media that participates in providing instructions to processor 104 for execution. Such a medium may take many forms, including but not limited to, non-volatile media, volatile media, and transmission media. Non-volatile media includes, for example, optical or magnetic disks, such as storage device 110. Volatile media includes dynamic memory, such as memory 106. Transmission media includes coaxial cables, copper wire, and fiber optics, including the wires that comprise bus 102.

Common forms of computer-readable media or computer program products include, for example, a floppy disk, a flexible disk, hard disk, magnetic tape, or any other magnetic medium, a CD-ROM, digital video disc (DVD), a Blu-ray Disc, any other optical medium, a thumb drive, a memory card, a RAM, PROM, and EPROM, a FLASH-EPROM, any other memory chip or cartridge, or any other tangible medium from which a computer can read.

Various forms of computer readable media may be involved in carrying one or more sequences of one or more instructions to processor 104 for execution. For example, the instructions may initially be carried on the magnetic disk of a remote computer. The remote computer can load the instructions into its dynamic memory and send the instructions over a telephone line using a modem. A modem local to computer system 100 can receive the data on the telephone line and use an infra-red transmitter to convert the data to an infra-red signal. An infra-red detector coupled to bus 102 can receive the data carried in the infra-red signal and place the data on bus 102. Bus 102 carries the data to memory 106, from which processor 104 retrieves and executes the instructions. The instructions received by memory 106 may optionally be stored on storage device 110 either before or after execution by processor 104.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

The following descriptions of various implementations of the present teachings have been presented for purposes of illustration and description. It is not exhaustive and does not limit the present teachings to the precise form disclosed. Modifications and variations are possible in light of the above teachings or may be acquired from practicing of the present teachings. Additionally, the described implementation includes software but the present teachings may be implemented as a combination of hardware and software or in hardware alone. The present teachings may be implemented with both object-oriented and non-object-oriented programming systems.

Resolution Saturation Detection

As described above, the ion detection system used with a time-of-flight (TOF) mass spectrometer, for example, can include an ion detector and an analog-to-digital converter (ADC). The ion detection system produces a sub-spectrum for each extraction of a plurality of ion extractions. Conventionally, a mass spectrum is obtained by combining (i.e., summing) the sub-spectra for the plurality of extractions.

This method works well up to a certain point. However, when a large number of ions of the same mass-to-charge ration (m/z) hit the detector at approximately the same time, resolution is decreased. As a result, it becomes difficult to resolve or observe nearby ions. This effect on the mass spectrum can be called resolution saturation.

Figure 2:
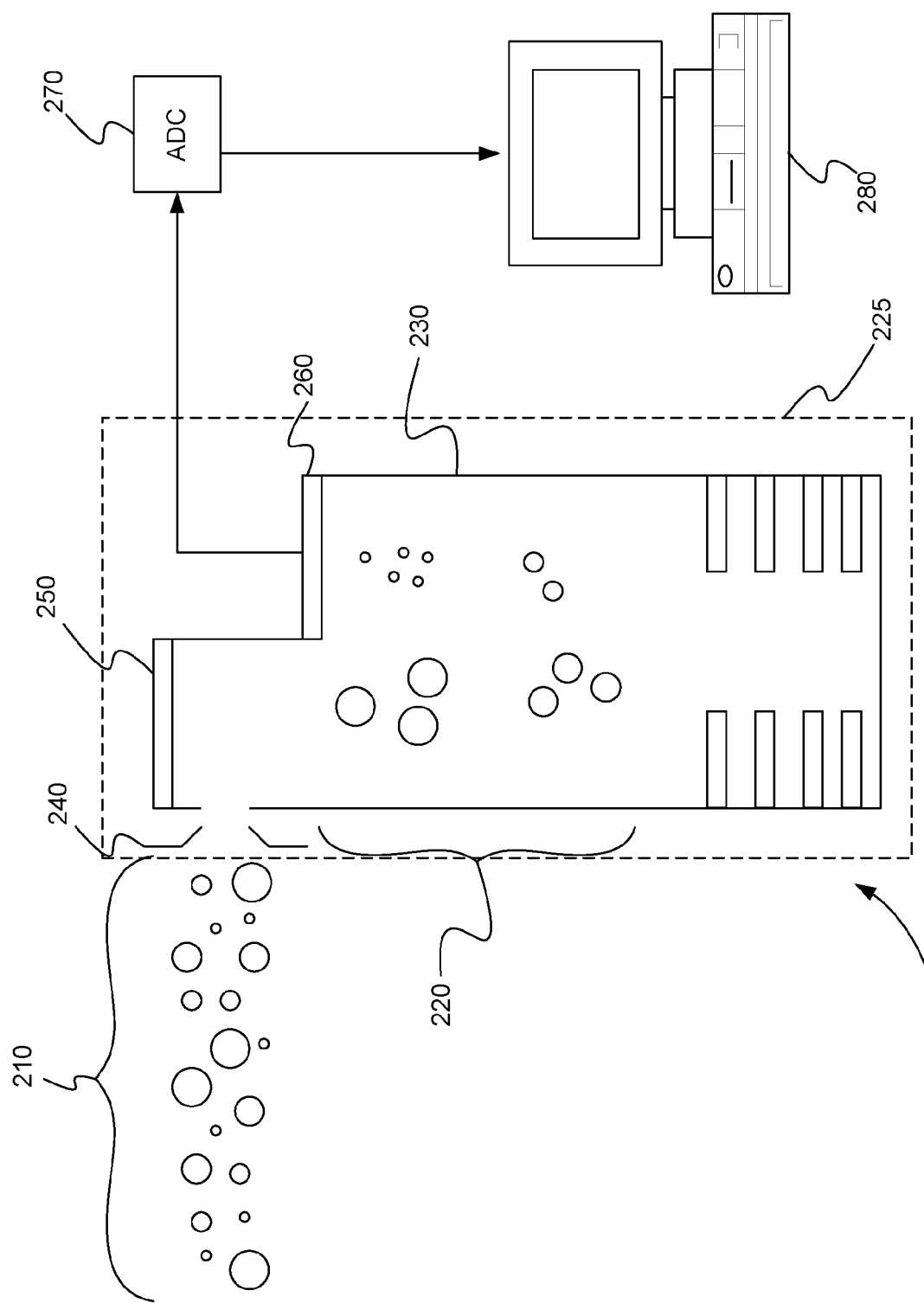
FIG. 2 is an exemplary diagram of a time-of-flight (TOF) mass spectrometry system showing ions entering a TOF tube, in accordance with various embodiments.

FIG. 2 is an exemplary diagram of a time-of-flight (TOF) mass spectrometry system 200 showing ions 210 entering TOF tube 230, in accordance with various embodiments. TOF mass spectrometry system 200 includes TOF mass spectrometer 225 and processor 280. TOF mass spectrometer 225 includes TOF tube 230, skimmer 240, extraction device 250, and ion detector 260. Skimmer 240 controls the number of ions entering TOF tube 230. Ions 210 are moving from an ion source (not shown) to TOF tube 230. The number of ions entering TOF tube 230 can be controlled by pulsing skimmer 240, for example.

Extraction device 250 imparts a constant energy to the ions that have entered TOF tube 230 through skimmer 240. Extraction device 250 imparts this constant energy by applying a fixed voltage at a fixed frequency, producing a series of extraction pulses, for example. Because each ion receives the same energy from extraction device 250, the velocity of each ion depends on its m/z. According to the equation for kinetic energy, velocity is proportional to the inverse square root of the m/z. As a result, lighter ions fly through TOF tube 230 much faster than heavier ions. Ions 220 are imparted with a constant energy in a single extraction, but fly through TOF tube 230 at different velocities.

Time is needed between extraction pulses to separate the ions in TOF tube 230 and detect them at ion detector 260. Enough time is allowed between extraction pulses so that the heaviest ion can be detected.

Ion detector 260 generates an electrical detection pulse for every ion that strikes it during an extraction. These detection pulses are passed to ADC 270, which records the amplitudes of the detected pulses digitally. ADC 270 is shown separately from TOF mass spectrometer 225. In various alternative embodiments, ADC 270 can be included in TOF mass spectrometer 225, or can be included as part of processor 280.

Processor 280 receives the amplitudes recorded by ADC detector subsystem 270 during each extraction. Because each extraction may contain only a few ions from a compound of interest, the responses for each extraction can be thought of as a sub-spectrum. In order to produce more useful results, processor 280 conventionally sums the sub-spectra of time values from a number of extractions to produce a full spectrum.

Figure 3:
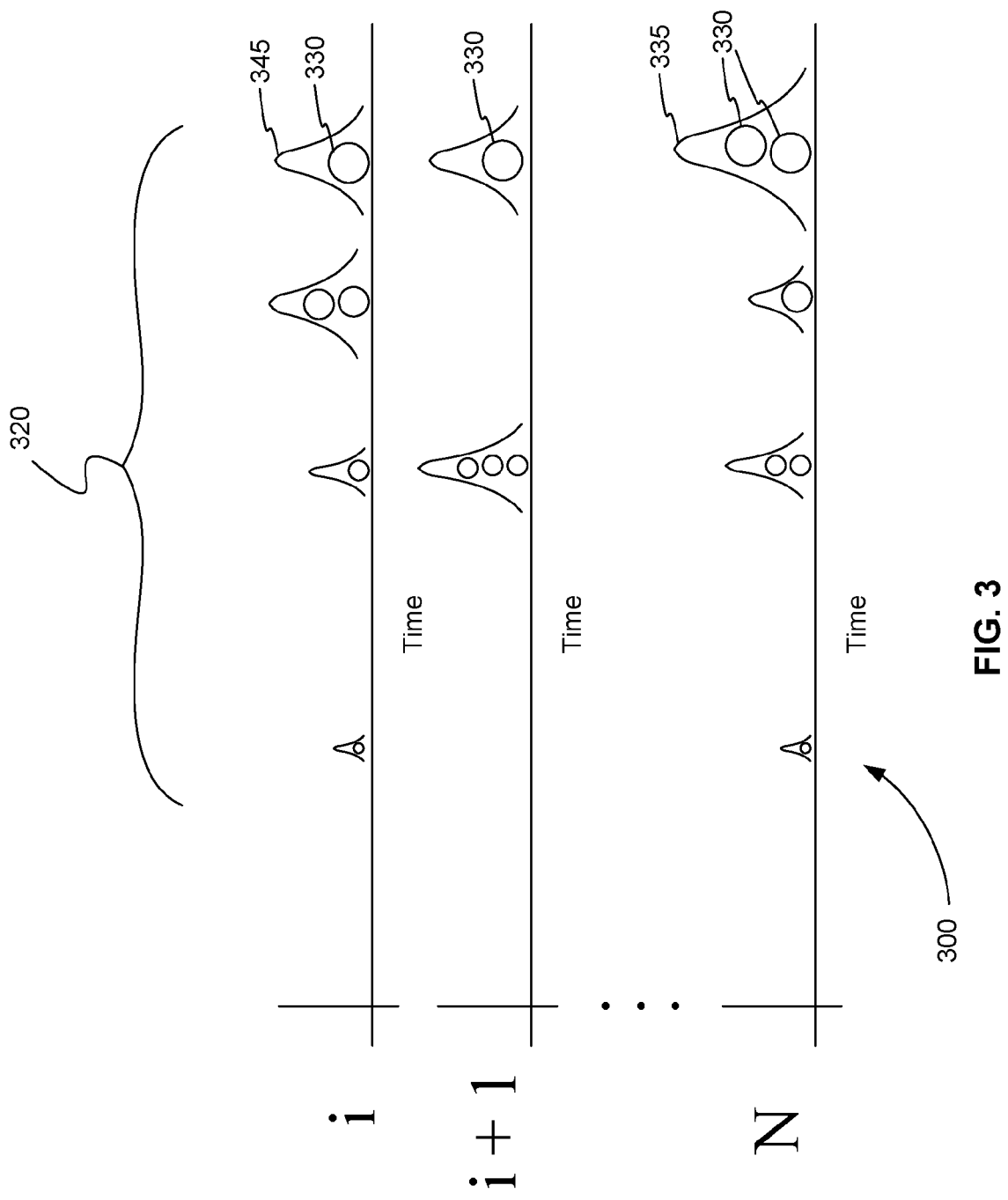
FIG. 3 is a plot of sub-spectra received by the processor of FIG. 2 for a series of N extractions, according to various embodiments.

FIG. 3 is a plot of sub-spectra 300 received by processor 280 of FIG. 2 for a series of N extractions, according to various embodiments. Sub-spectra for extractions i through N include time values for each ion detected. The horizontal position of each ion in each sub-spectrum represents the time it takes that ion to be detected relative to the extraction pulse. Ions 320 of extraction i in FIG. 3 correspond to ions 220 in FIG. 2, for example.

Ions of the same m/z can arrive at the detector at substantially the same time. For example, ions 330 are ions that have the same m/z. In extraction i+2, ions 330 hit the detector at substantially the same time. Ideally, ions of the same m/z should arrive at the detector at the same time. In practice, a number of factors contribute to slightly different times for ions of the same m/z. One factor is the starting point of the ions. If one ion has a shorter distance to travel than another ion of the same m/z, then the ion with the shorter distance will arrive earlier. Another factor is a component of velocity in another direction. If one ion starts with a component of velocity in a direction that another ion of the same m/z does not have, the two ions are unlikely to arrive at exactly the same time. As a result, ions of the same m/z arrive at the detector at slightly different times.

A key aspect of various embodiments is determining an estimate of the number of ions hitting the detector at the same time. As shown in sub-spectra 300 of FIG. 3, an ADC produces an amplitude response that is dependent on the number of ions hitting the detector at substantially the same time. For example, the two ions 330 in extraction N produce amplitude response 335 that is larger than amplitude response 345, which is produced by a single ion 330 in extraction i. In other words, the response that an ADC produces is proportional to the number of ions hitting the detector at substantially the same time. This proportionality holds for smaller numbers of ions hitting the detector at substantially the same time. However, for larger numbers of ions hitting the detector at substantially the same time the relationship becomes non-linear. Conventionally, the sub-spectra represented by the N extractions in FIG. 3 are combined to produce a spectrum.

Figure 4:
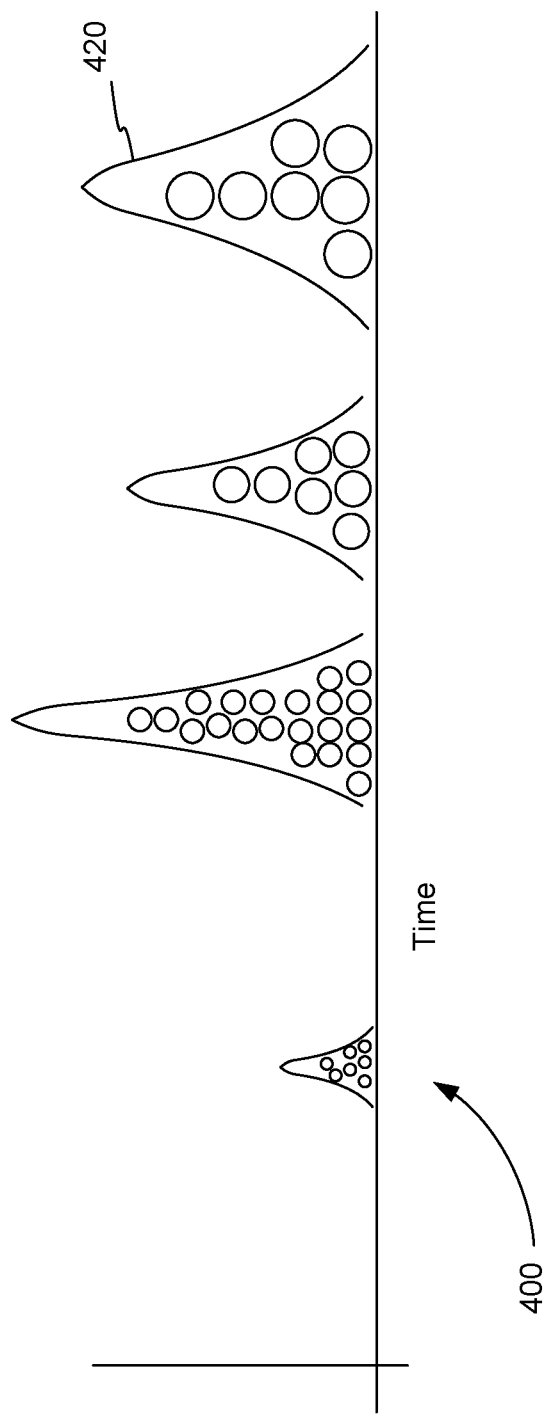
FIG. 4 is a plot of the ADC spectrum produced by the processor of FIG. 2 from summing the N sub-spectra of FIG. 3, in accordance with various embodiments.

FIG. 4 is a plot of the ADC spectrum 400 produced by processor 280 of FIG. 2 from summing the N sub-spectra of FIG. 3, in accordance with various embodiments. Spectrum 400 of FIG. 4 includes ions of four different m/z values. For example, the peaks of ions 330 from the N extractions in FIG. 3 are combined as peak 420 of FIG. 4.

As described above, however, the amplitude an ADC TOF detector produces for ions of a certain m/z does not remain linear as the count, or number of ions arriving at the detector at the same time, increases. For any average ion flux, the measured intensities have a more or less Gaussian distribution about a mean value. The mean number of ions detected for a certain m/z is, for example, n. If n is 2, the mean is shifted higher than if n is 1, but there is an overlap. The response of the detector stays linear until n is about 15. At this point, quantitation is still accurate and peak position is still accurate (mass accuracy). However, it may not be possible to resolve nearby ions even though the resolution observed appears high enough to do so. The resolution observed is calculated, for example, by dividing the m/z by the peak width at half height (WHH).

Figure 5:
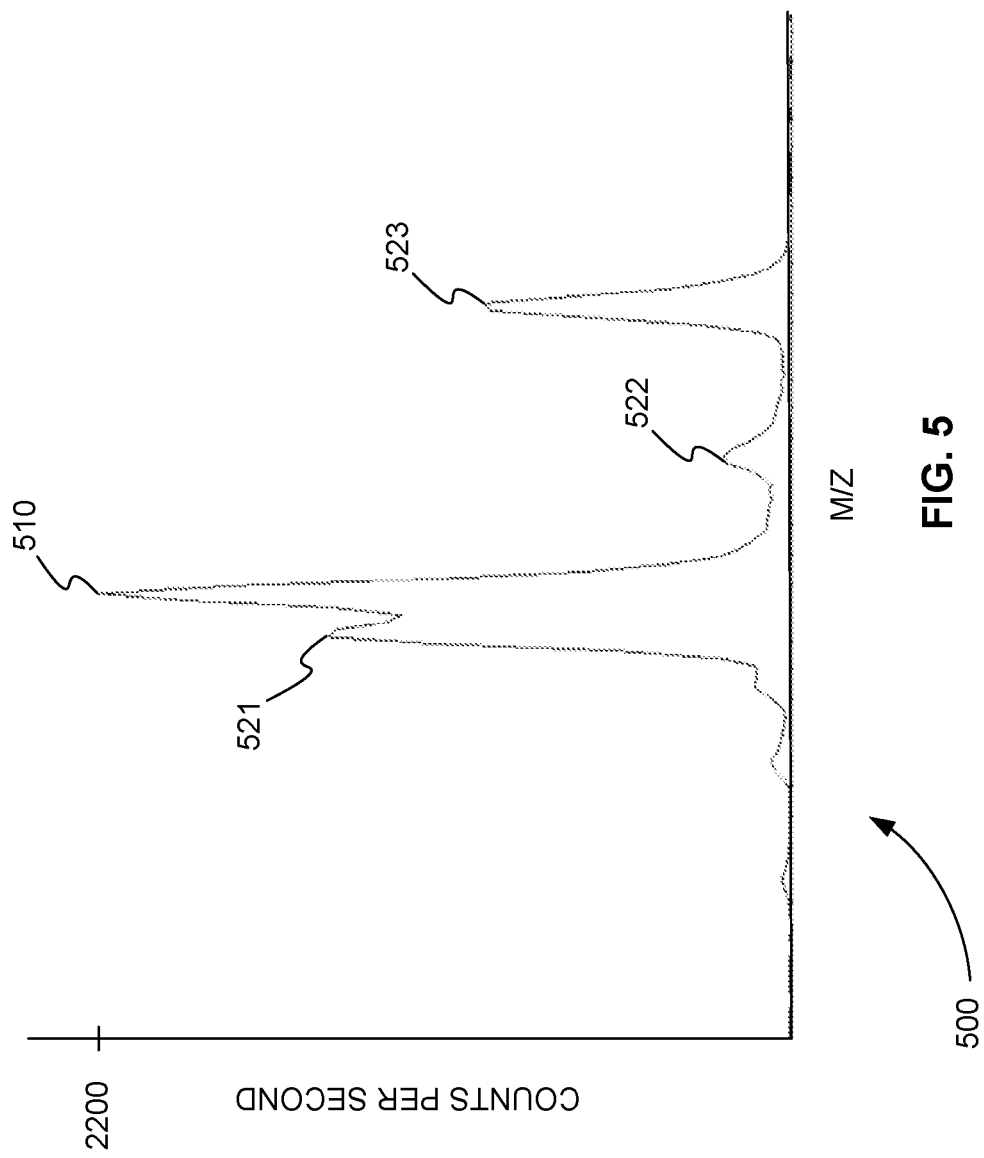
FIGS. 5-7 are a series of plots showing how a peak is convolved with nearby peaks as the number of ions hitting the detector at approximately the same time in that peak increases, in accordance with various embodiments.
Figure 6:
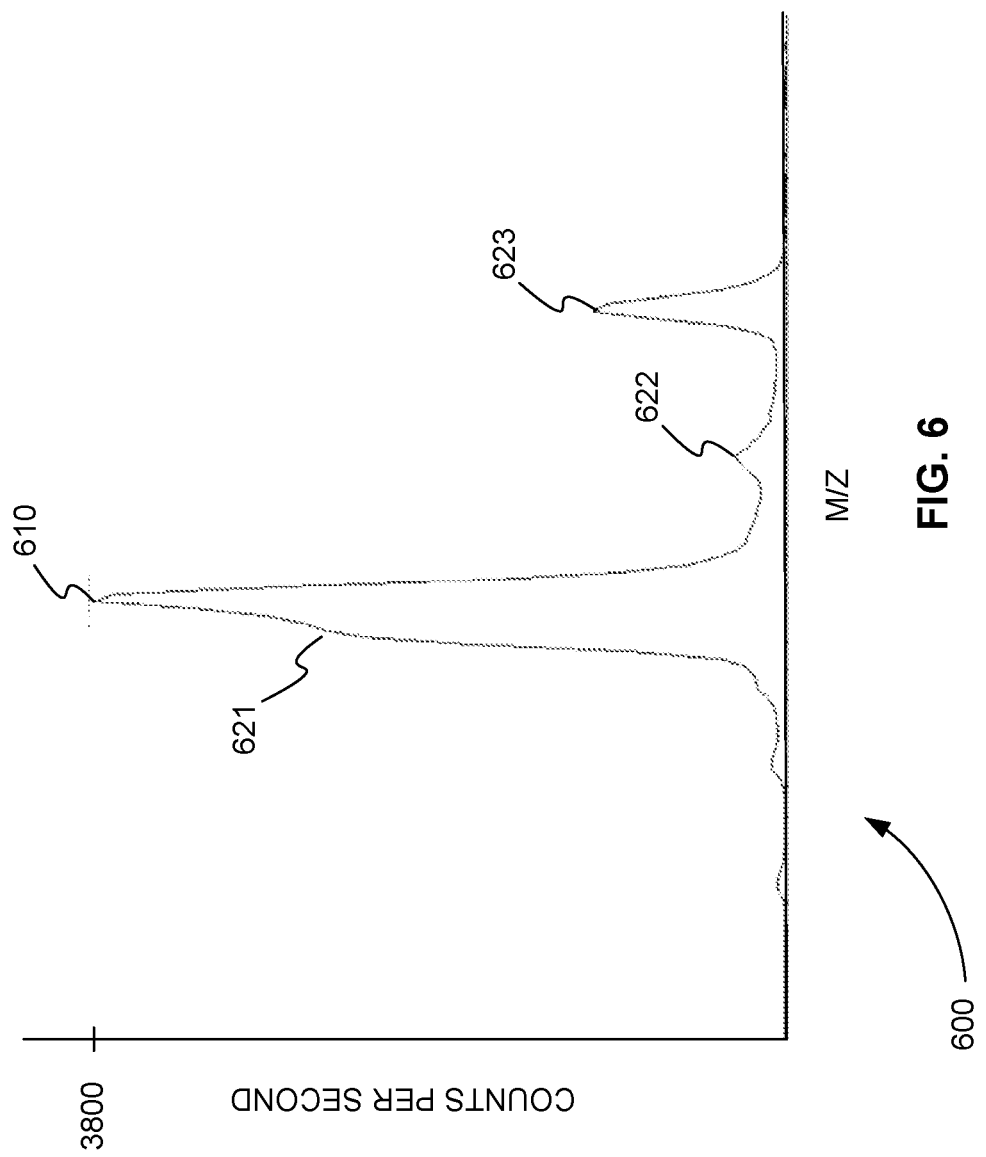
Figure 7:
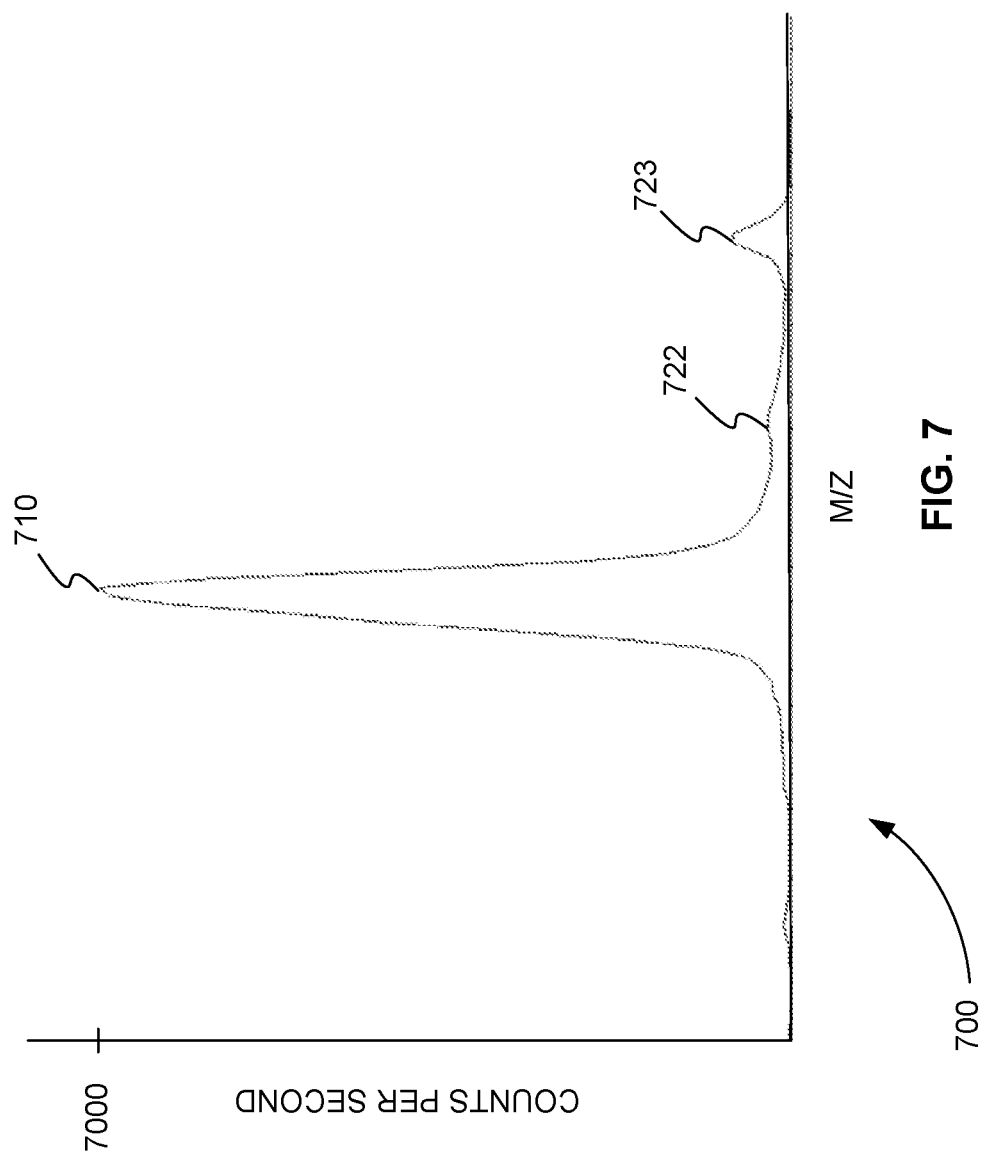

FIGS. 5-7 are a series of plots 500, 600 and 700 showing how a peak is convolved with nearby peaks as the number of ions hitting the detector at approximately the same time in that peak increases, in accordance with various embodiments. In plot 500 of FIG. 5, peak 510 contains a small number of ions of m/z M that hit the detector at the same time. Potential nearby interfering peaks 521, 522, and 523 are readily apparent. In plot 600 of FIG. 6, peak 610 contains a larger number of ions of m/z M that hit the detector at the same time. Note that peak 610 has a higher amplitude than peak 510 of FIG. 5. Interfering peaks 621, 622, and 623 of FIG. 6 start to convolve into peak 610. In plot 700 of FIG. 7, peak 710 contains a still larger number of ions of m/z M that hit the detector at the same time. Note that peak 710 has a higher amplitude than peak 610 of FIG. 6. The interfering peak corresponding to peak 521 in FIGS. 5 and 621 in FIG. 6 has completely convolved into peak 710 of FIG. 7. In addition, interfering peaks 722 and 723 have convolved further into peak 710, which is now also narrower than the entire group at lower intensities, that is, peak 710 appears to have higher resolution.

This convolution of nearby peaks shown in FIGS. 5-7 is caused by resolution saturation. In other words, as more ions of the same m/z hit the detector at the same time, the observed resolution increases, but nearby ions cannot be resolved. Observed resolution is calculated, for example, by dividing the m/z by the width of the pulse at half height (WHH). Due to this convolution, it may not be possible to detect convolved peaks when resolution saturation occurs.

System for Grouping and Combining Amplitudes

In various embodiments, convolved peaks due to resolution saturation can be detected by grouping and combining sub-spectra of extractions based on the amplitudes of the ions hitting the detector at the same time. Returning to FIG. 2, system 200 can be used for grouping and combining amplitudes for a selected ion m/z from TOF sub-spectra based on the number of ions at the ion m/z hitting the detector at the same time in order to detect convolution.

An ion source (not shown) ionizes sample molecules producing a beam of ions. TOF mass spectrometer 225 that includes detector 260 performs a plurality of ion extractions on the beam of ions. ADC 270 receives electrical detections from detector 260 and, during each extraction, measures the amplitudes of the ions hitting the detector over time. A mass sub-spectrum is produced for each extraction of the plurality of ion extractions.

Processor 280 can be, but is not limited to, a computer, microprocessor, or any device capable of sending and receiving control signals and data to and from TOF mass spectrometer 225 and processing data. Processor 280 is, for example, a computer system such as the computer system shown in FIG. 1. Processor 280 is in communication with TOF mass spectrometer 225 and ADC 270.

Processor 280 receives the plurality of mass sub-spectra. Processor 280 selects an ion m/z from the plurality of mass sub-spectra. In various embodiments, processor 280 selects an ion m/z by comparing each amplitude in one or more mass sub-spectra of the plurality of mass sub-spectra to a predetermined amplitude threshold and selecting the ion m/z that has an amplitude that exceeds the predetermined amplitude threshold.

For each mass sub-spectrum of the plurality of mass sub-spectra, processor 280 assigns the amplitude and m/z of an ion within a m/z tolerance of the ion m/z to a corresponding amplitude band of a plurality of predetermined amplitude bands. For each amplitude band of the plurality of predetermined amplitude bands, processor 280 combines the plurality of amplitude and m/z values into a peak, resulting in a plurality of peaks corresponding to the plurality of predetermined amplitude bands.

In various embodiments, for each amplitude band of the plurality of predetermined amplitude bands, processor 280 combines the plurality of sub-spectra into a peak by counting the number of amplitudes at each m/z in the plurality of amplitude and m/z values. A histogram that describes the number of observed amplitudes with respect to m/z is produced. Finally, processor 280 calculates a peak for the histogram, resulting in a plurality of peaks corresponding to the plurality of predetermined amplitude bands.

Figure 8:
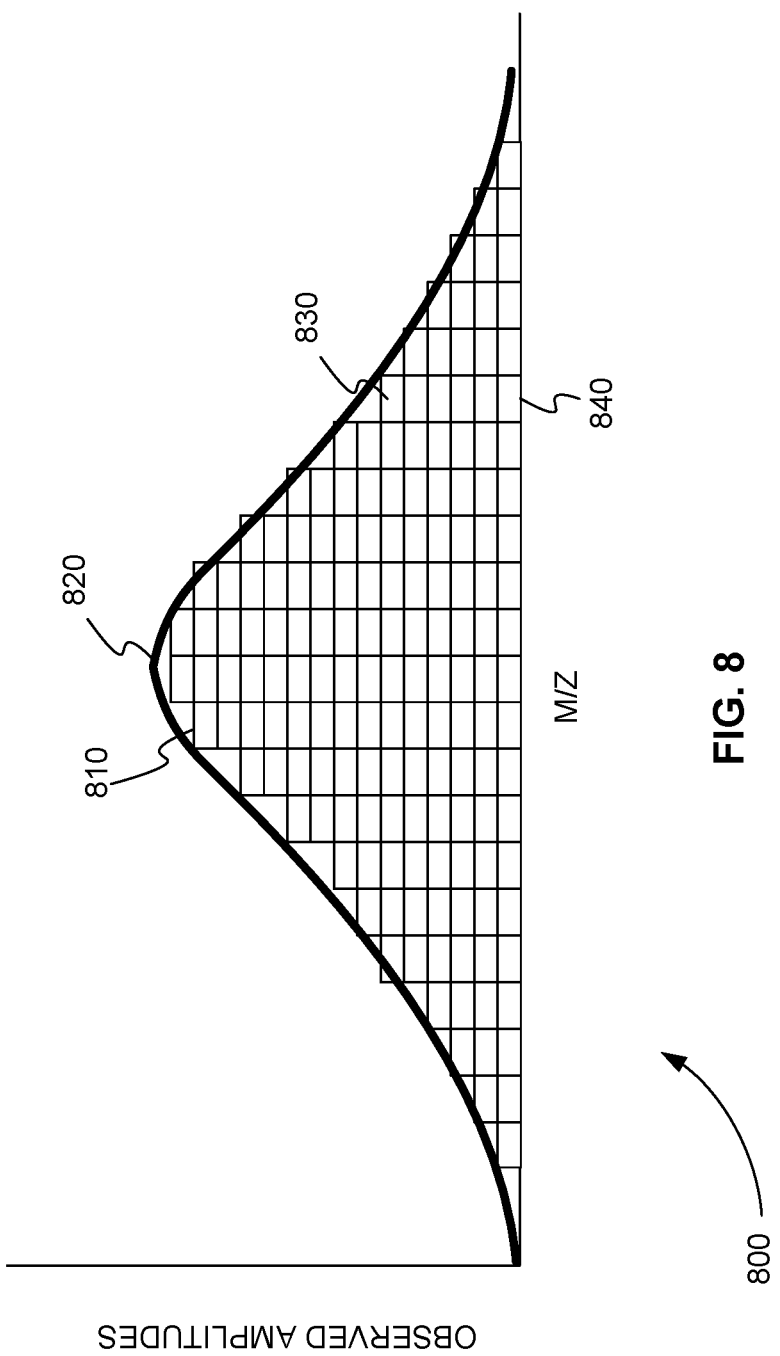
FIG. 8 is an exemplary plot of a histogram of observed amplitudes with respect to mass-to-charge ration (m/z) of an amplitude band and a calculated peak 820 for the amplitude band, in accordance with various embodiments.

FIG. 8 is an exemplary plot 800 of a histogram 810 of observed amplitudes with respect to m/z of an amplitude band and a calculated peak 820 for the amplitude band, in accordance with various embodiments. Peak 820 is calculated from histogram 810. Rectangles 830 represent observations of amplitudes at m/z 840, for example. So, there are six observations of amplitudes at m/z 840.

Figure 9:
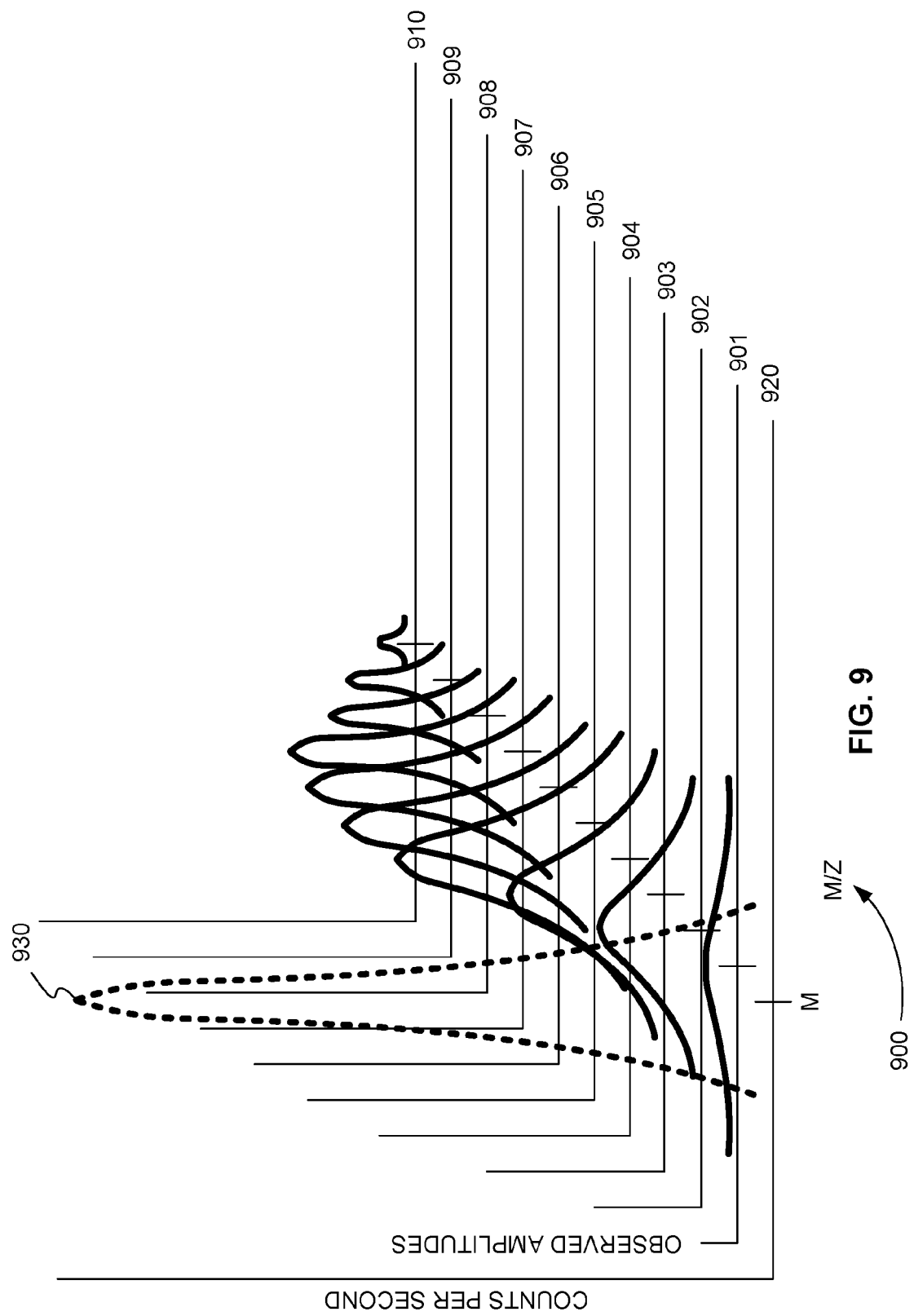
FIG. 9 is a superposition of a conventional mass spectrum showing a peak for an ion m/z without convolution and a number of plots of peaks for amplitude bands that represent increasing numbers of ions with the same ion m/z hitting the detector at the same time, in accordance with various embodiments.

FIG. 9 is superposition 900 of a conventional mass spectrum 920 showing a peak 930 for an ion m/z without convolution and plots 901-910 of peaks for amplitude bands that represent increasing numbers of ions with the same ion m/z hitting the detector at the same time, in accordance with various embodiments. Peak 930 is for a pure compound, for example.

Figure 10:
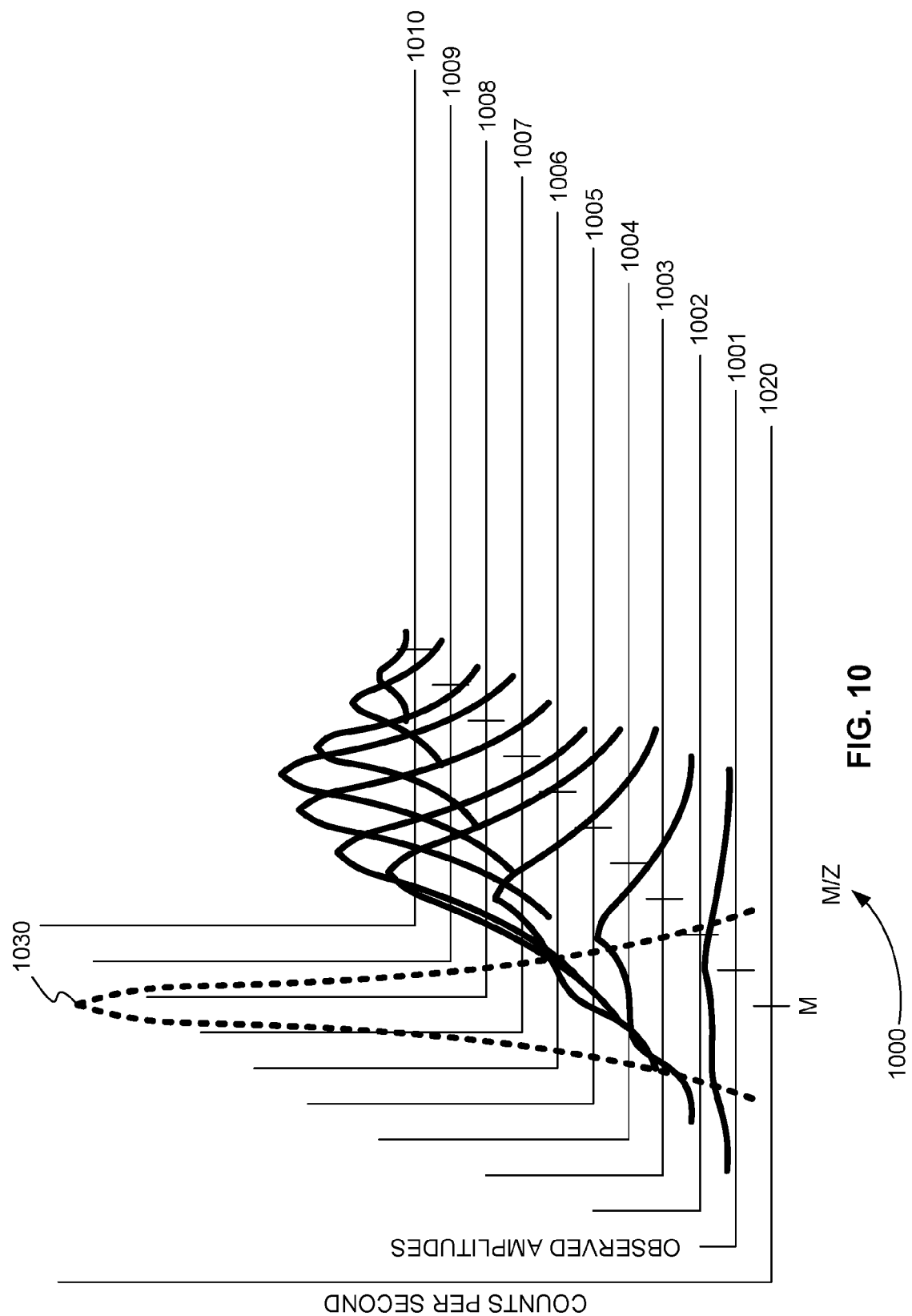
FIG. 10 is a superposition of a conventional mass spectrum showing a peak for an ion m/z with convolution and a number of plots of peaks for amplitude bands that represent increasing numbers of ions with the same ion m/z hitting the detector at the same time, in accordance with various embodiments.

FIG. 10 is superposition 1000 of a conventional mass spectrum 1020 showing a peak 1030 for an ion m/z with convolution and plots 1001-1010 of peaks for amplitude bands that represent increasing numbers of ions with the same ion m/z hitting the detector at the same time, in accordance with various embodiments. Peak 1030 is for a mixture of at least two different compounds that are very close in m/z, for example.

A comparison of peak 930 in FIG. 9 and peak 1030 in FIG. 10 shows the problem that can be produced by resolution saturation. Because a large number of ions from the compound at m/z M hit the detector at the same time the convolved peak of the other compound in the mixture is not apparent. As a result, peak in FIG. 10 is indistinguishable from peak 930 in FIG. 9, which is the peak for the pure compound at m/z M.

Using the peaks in plots 1001-1010 in FIG. 10, however, the convolution of peak 1030 can be uncovered. In accordance with various embodiments, this convolution can be uncovered from these peaks in, at least, three different ways.

First, the resolution of a peak representing a peak group can be compared to the expected resolution. Returning to FIG. 2, processor 280 further selects a peak from the plurality of peaks. In various embodiments, processor 280 selects the peak from the plurality of peaks that was calculated from an amplitude band of the plurality of predetermined amplitude bands having the largest number of amplitude and m/z values. Processor 280 picks the peak in plots 1005 or 1006 of FIG. 10, for example.

Processor 280 then calculates a resolution of the selected peak. In various embodiments, the resolution is calculated by dividing the m/z by the width of the peak measured at half height. Processor 280 compares the calculated resolution to a predetermined expected resolution of a non-convolved peak at the same m/z as the peak. Finally, processor 280 determines that the peak is convolved if the calculated resolution is less than a predetermined expected resolution by more than a predetermined resolution threshold. The resolutions of the peaks in plots 1005 or 1006 of FIG. 10 would be less than the predetermined expected resolution by more than a predetermined resolution threshold, for example. This can be seen by comparing the peaks in plots 905 and 906 of FIG. 9 with the peaks in plots 1005 or 1006 of FIG. 10. The peaks in plots 1005 or 1006 of FIG. 10 have greater widths than the corresponding peaks in plots 905 and 906 of FIG. 9. Since resolution is inversely proportional to width, the peaks in plots 1005 or 1006 of FIG. 10 have lower resolution than the corresponding peaks in plots 905 and 906 of FIG. 9.

A second method of uncovering convolution from peaks of amplitude bands involves comparing the offsets or centroid m/z values of the peaks. Returning to FIG. 2, processor 280 calculates a centroid m/z of each peak of the plurality of peaks, producing a plurality of centroid m/z values. Processor 280 then compares each centroid m/z of the plurality of centroid m/z values to each other. Finally, processor 280 determines that a peak of the plurality of peaks is convolved if any centroid m/z of the plurality of centroid m/z values differs from any other centroid m/z of the plurality of centroid m/z values by more than a predetermined m/z threshold.

For example, in FIG. 10 centroid m/z values are calculated for the peaks in plots 1001-1010. These m/z values are then compared to one another. If any of the centroid m/z values differs from any other centroid m/z by more than a predetermined m/z threshold, convolution is found. Convolution would be found in FIG. 10 by comparing the centroid m/z values of the peaks in plots 1001 and 1010, for example.

Finally, a third method of uncovering convolution from peaks of amplitude bands involves finding convolved peaks within the peaks. Returning to FIG. 2, processor 280 executes a peak finding algorithm that can identify convolution on one or more of the plurality of peaks to determine if a peak is comprised of more than one component. Processor 280 determines that a peak of the plurality of peaks is convolved, if the peak finding algorithm finds additional peak components in a lower amplitude band that are not observed in higher amplitude bands. Convolution would be found in FIG. 10 by executing a peak finding algorithm on the peaks in plots 1001-1010, for example. The peaks in these plots show peaks that are clearly convolved in the peaks for higher amplitude bands (1005-1010). In contrast, the peaks in plots 1001-1003 show at least two peak components in each peak.

Method for Grouping and Combining Amplitudes

Figure 11:
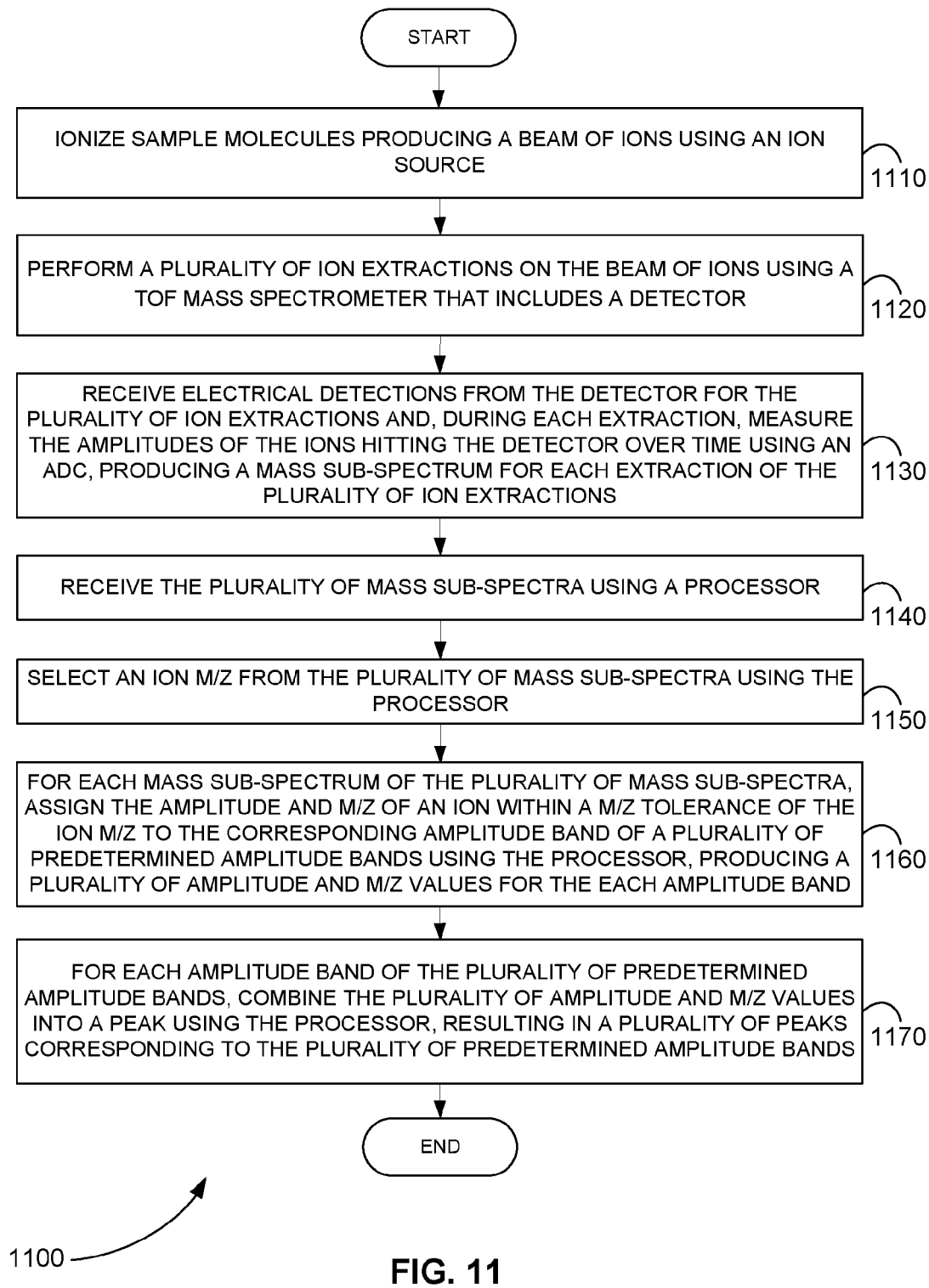
FIG. 11 is an exemplary flowchart showing a method for grouping and combining amplitudes for a selected ion m/z from TOF sub-spectra in order to detect convolution, in accordance with various embodiments.

FIG. 11 is an exemplary flowchart showing a method 1100 for grouping and combining amplitudes for a selected ion m/z from TOF sub-spectra in order to detect convolution, in accordance with various embodiments.

In step 1110 of method 1100, sample molecules are ionized producing a beam of ions using an ion source.

In step 1120, a plurality of ion extractions are performed on the beam of ions using a TOF mass spectrometer that includes a detector.

In step 1130, electrical detections from the detector for the plurality of ion extractions are received and, during each extraction, the amplitudes of the ions hitting the detector over time are measured using an analog-to-digital converter (ADC), producing a mass sub-spectrum for each extraction of the plurality of ion extractions.

In step 1140, the plurality of mass sub-spectra are received using a processor.

In step 1150, an ion m/z from the plurality of mass sub-spectra is selected using the processor.

In step 1160, for each mass sub-spectrum of the plurality of mass sub-spectra, the amplitude and m/z of an ion within a m/z tolerance of the ion m/z is assigned to the corresponding amplitude band of a plurality of predetermined amplitude bands using the processor, producing a plurality of amplitude and m/z values for the each amplitude band.

In step 1170, for each amplitude band of the plurality of predetermined amplitude bands, the plurality of amplitude and m/z values are combined into a peak using the processor, resulting in a plurality of peaks corresponding to the plurality of predetermined amplitude bands.

Computer Program Product for Grouping and Combining Amplitudes

In various embodiments, computer program products include a tangible computer-readable storage medium whose contents include a program with instructions being executed on a processor so as to perform a method for grouping and combining amplitudes for a selected ion m/z from TOF sub-spectra in order to detect convolution. This method is performed by a system that includes one or more distinct software modules.

Figure 12:
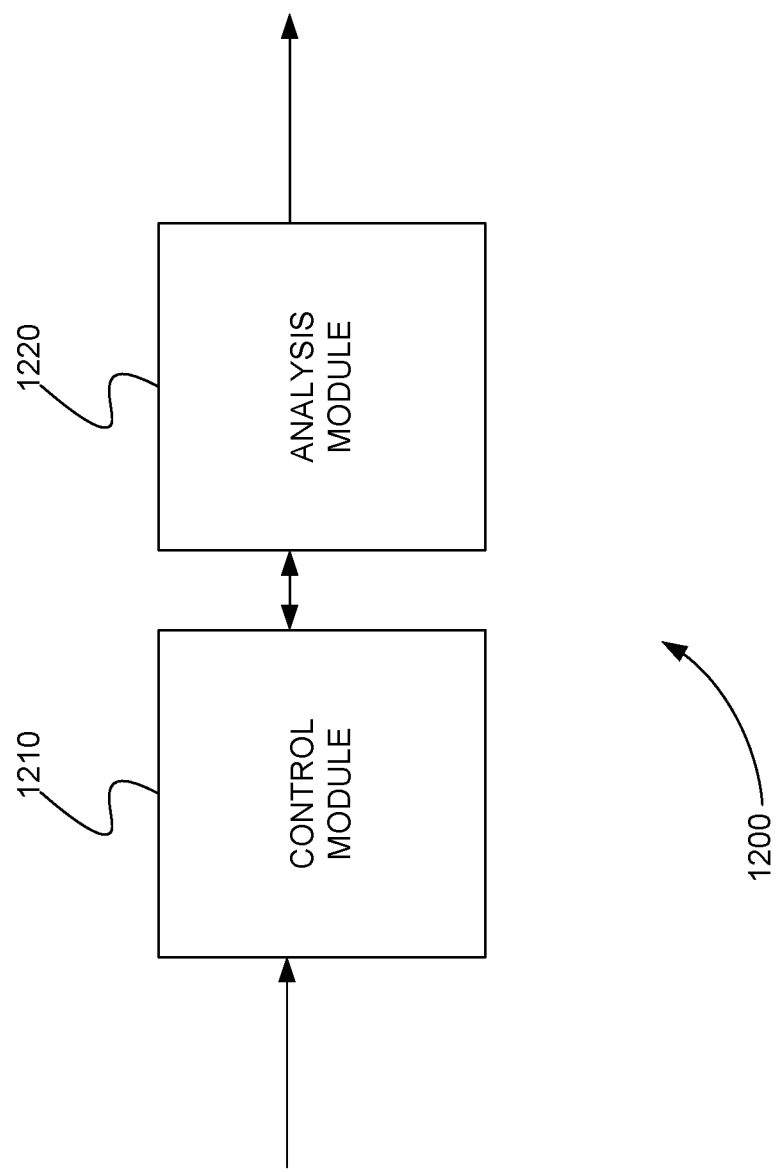
FIG. 12 is a schematic diagram of a system that includes one or more distinct software modules that performs a method for grouping and combining amplitudes for a selected ion m/z from TOF sub-spectra in order to detect convolution, in accordance with various embodiments.

FIG. 12 is a schematic diagram of a system 1200 that includes one or more distinct software modules that performs a method for grouping and combining amplitudes for a selected ion m/z from TOF sub-spectra in order to detect convolution, in accordance with various embodiments. System 1200 includes control module 1210 and analysis module 1220.

Control module 1210 instructs an ion source to ionize sample molecules producing a beam of ions. Control module 1210 instructs a TOF mass spectrometer that includes a detector to perform a plurality of ion extractions on the beam of ions. Control module 1210 instructs an ADC to receive electrical detections from the detector for the plurality of ion extractions and, during each extraction, measure the amplitudes of the ions hitting the detector over time, producing a mass sub-spectrum for each extraction of the plurality of ion extractions.

Analysis module 1220 receives the plurality of mass sub-spectra. Analysis module 1220 selects an ion m/z from the plurality of mass sub-spectra. For each mass sub-spectrum of the plurality of mass sub-spectra, analysis module 1220 assigns the amplitude and m/z of an ion within a m/z tolerance of the ion m/z to the corresponding amplitude band of a plurality of predetermined amplitude bands, producing a plurality of amplitude and m/z values for the each amplitude band. For each amplitude band of the plurality of predetermined amplitude bands, analysis module 1220, combines the plurality of amplitude and m/z values into a peak, resulting in a plurality of peaks corresponding to the plurality of predetermined amplitude bands.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

What is claimed is:

1. A system for grouping and combining amplitudes for a selected ion mass-to-charge ratio (m/z) from time-of-flight (TOF) sub-spectra in order to detect convolution, comprising:
   an ion source that ionizes sample molecules producing a beam of ions;
   a TOF mass spectrometer that includes a detector and performs a plurality of ion extractions on the beam of ions;
   an analog-to-digital converter (ADC) that receives electrical detections from the detector and, during each extraction, measures the amplitudes of the ions hitting the detector over time, producing a mass sub-spectrum for each extraction of the plurality of ion extractions; and
   a processor in communication with the TOF mass spectrometer and the ADC that receives the plurality of mass sub-spectra;
      selects an ion m/z from the plurality of mass sub-spectra;
      for each mass sub-spectrum of the plurality of mass sub-spectra, assigns the amplitude and m/z of an ion within a m/z tolerance of the ion m/z to the corresponding amplitude band of a plurality of predetermined amplitude bands, producing a plurality of amplitude and m/z values for the each amplitude band; and
      for each amplitude band of the plurality of predetermined amplitude bands, combines the plurality of amplitude and m/z values into a peak, resulting in a plurality of peaks corresponding to the plurality of predetermined amplitude bands.

2. The system of claim 1, wherein the processor selects an ion m/z by
   comparing each amplitude in one or more mass sub-spectra of the plurality of mass sub-spectra to a predetermined amplitude threshold and
   selecting the ion m/z that has an amplitude that exceeds the predetermined amplitude threshold.

3. The system of claim 1, wherein the processor, for each amplitude band of the plurality of predetermined amplitude bands, combines the plurality of amplitude and m/z values into a peak by
   counting the number of amplitudes at each m/z of the plurality of amplitude and m/z values, producing a histogram that describes the number of observed amplitudes with respect to m/z, and
   calculating a peak for the histogram, resulting in a plurality of peaks corresponding to the plurality of predetermined amplitude bands.

4. The system of claim 1, wherein the processor further selects a peak from the plurality of peaks,
   calculates a resolution of the peak,
   compares the calculated resolution to a predetermined expected resolution of a non-convolved peak at the same m/z as the peak, and
   determines that the peak is convolved if the calculated resolution is less than the predetermined expected resolution by more than a predetermined resolution threshold.

5. The system of claim 4, wherein the resolution is calculated by dividing the m/z of the peak by the width of the peak at half height.

6. The system of claim 4, wherein the processor selects the peak having the largest number of amplitude and m/z values from the plurality of peaks that was calculated from an amplitude band of the plurality of predetermined amplitude bands.

7. The system of claim 1, wherein the processor further calculates a centroid m/z of each peak of the plurality of peaks, producing a plurality of centroid m/z values,
   compares each centroid m/z of the plurality of centroid m/z values to each other, and
   determines that a peak of the plurality of peaks is convolved if any centroid m/z of the plurality of centroid m/z values differs from any other centroid m/z of the plurality of centroid m/z values by more than a predetermined m/z threshold.

8. The system of claim 1, wherein the processor further executes a peak finding algorithm on each peak of the plurality of peaks to determine if the peak is comprised of more than one component.

9. The system of claim 1, further comprising
   calculating a centroid m/z of each peak of the plurality of peaks, producing a plurality of centroid m/z values using the processor,
   comparing each centroid m/z of the plurality of centroid m/z values to each other using the processor, and
   determining that a peak of the plurality of peaks is convolved if any centroid m/z of the plurality of centroid m/z values differs from any other centroid m/z of the plurality of centroid m/z values by more than a predetermined m/z threshold using the processor.

10. A method for grouping and combining amplitudes for a selected ion mass-to-charge ratio (m/z) from time-of-flight (TOF) sub-spectra in order to detect convolution, comprising:
   ionizing sample molecules producing a beam of ions using an ion source;
   performing a plurality of ion extractions on the beam of ions using a TOF mass spectrometer that includes a detector;
   receiving electrical detections from the detector for the plurality of ion extractions and, during each extraction, measuring the amplitudes of the ions hitting the detector over time using an analog-to-digital converter (ADC), producing a mass sub-spectrum for each extraction of the plurality of ion extractions;
   receiving the plurality of mass sub-spectra using a processor;
   selecting an ion m/z from the plurality of mass sub-spectra using the processor;
   for each mass sub-spectrum of the plurality of mass sub-spectra, assigning the amplitude and m/z of an ion within a m/z tolerance of the ion m/z to the corresponding amplitude band of a plurality of predetermined amplitude bands using the processor, producing a plurality of amplitude and m/z values for the each amplitude band; and for each amplitude band of the plurality of predetermined amplitude bands, combining the plurality of amplitude and m/z values into a peak using the processor, resulting in a plurality of peaks corresponding to the plurality of predetermined amplitude bands.

11. The method of claim 10, wherein selecting an ion m/z comprises comparing each amplitude in one or more mass sub-spectra of the plurality of mass sub-spectra to a predetermined amplitude threshold and selecting the ion m/z that has an amplitude that exceeds the predetermined amplitude threshold.

12. The method of claim 10, wherein for each amplitude band of the plurality of predetermined amplitude bands, combining the plurality of amplitude and m/z values into a peak comprises counting the number of amplitudes at each m/z of the plurality of amplitude and m/z values, producing a histogram that describes the number of observed amplitudes with respect to m/z, and calculating a peak for the histogram, resulting in a plurality of peaks corresponding to the plurality of predetermined amplitude bands.

13. The method of claim 10, further comprising selecting a peak from the plurality of peaks using the processor, calculating a resolution of the peak using the processor, comparing the calculated resolution to a predetermined expected resolution of a non-convolved peak at the same m/z as the peak using the processor, and determining that the peak is convolved if the calculated resolution is less than the predetermined expected resolution by more than a predetermined resolution threshold using the processor.

14. The method of claim 13, wherein selecting the peak comprises selecting a peak having the largest number of amplitude and m/z values from the plurality of peaks that was calculated from an amplitude band of the plurality of predetermined amplitude bands.

15. A computer program product, comprising a non-transitory and tangible computer-readable storage medium whose contents include a program with instructions being executed on a processor so as to perform a method for grouping and combining amplitudes for a selected ion mass-to-charge ratio (m/z) from time-of-flight (TOF) sub-spectra in order to detect convolution, the method comprising:

providing a system, wherein the system comprises one or more distinct software modules, and wherein the distinct software modules comprise a control module and an analysis module;

instructing an ion source to ionize sample molecules producing a beam of ions using the control module;

instructing a TOF mass spectrometer that includes a detector to perform a plurality of ion extractions on the beam of ions using the control module;

instructing an analog-to-digital converter (ADC) to receive electrical detections from the detector for the plurality of ion extractions and, during each extraction, measure the amplitudes of the ions hitting the detector over time using the control module, producing a mass sub-spectrum for each extraction of the plurality of ion extractions;

receiving the plurality of mass sub-spectra using the analysis module;

selecting an ion m/z from the plurality of mass sub-spectra using the analysis module;

for each mass sub-spectrum of the plurality of mass sub-spectra, assigning the amplitude and m/z of an ion within a m/z tolerance of the ion m/z to the corresponding amplitude band of a plurality of predetermined amplitude bands using the analysis module, producing a plurality of amplitude and m/z values for the each amplitude band; and for each amplitude band of the plurality of predetermined amplitude bands, combining the plurality of amplitude and m/z values into a peak using the analysis module, resulting in a plurality of peaks corresponding to the plurality of predetermined amplitude bands.

* * * * *